(12) United States Patent
Machida et al.

(10) Patent No.: US 6,852,833 B1
(45) Date of Patent: Feb. 8, 2005

(54) ARTIFICIAL CHAPERON KIT

(75) Inventors: Sachiko Machida, Tsukuba (JP); Kiyoshi Hayashi, Tsuchiura (JP)

(73) Assignees: Director of National Food Research Institute, Ministry of Agriculture, Forestry and Fisheries, Tsukuba (JP); Bio-oriented Technology Research Advancement Institution, Saitama-ken (JP)

( * ) Notice: Subject to any disclaimer, the term of this patent is extended or adjusted under 35 U.S.C. 154(b) by 464 days.

(21) Appl. No.: 09/635,429

(22) Filed: Aug. 10, 2000

(30) Foreign Application Priority Data

Mar. 15, 2000 (JP) ........................................ 2000-071533

(51) Int. Cl.⁷ ............................. C07K 1/00; C09F 1/02; C07H 1/00
(52) U.S. Cl. ....................... 530/350; 530/211; 530/395; 530/412; 530/419; 530/422; 435/97; 435/810; 536/126; 536/127
(58) Field of Search ................................ 530/350, 211, 530/395, 412, 419, 422; 435/97, 810; 536/126, 127

(56) References Cited

PUBLICATIONS

Daugherty et al., The Journal of Biological Chemistry, vol. 273, No. 51, pp. 33961–33971, Dec. 18, 1998.*
Takaha et al., The Journal of Biological Chemistry, vol. 271, No. 6, pp. 2902–2908, Feb. 9, 1996.*
Sundari et al., FEBS Letters, vol. 443, pp. 215–219, 1999.*
Machida et al., FEBS Letters, vol. 486, pp. 131–135, 2000.*
Daugherty et al. The Journal of Biological Chemistry, Vo. 273, No. 51, pp. 33961–33971. Dec. 18, 1988.*
Kitamura et al. Macromol. Rapid Commun., vol. 20, pp. 612–615, 1999.*
Larsen et al. Carbohydrate Research, vol. 309, pp. 153–159, 1998.*

* cited by examiner

*Primary Examiner*—Jon Weber
*Assistant Examiner*—Abdel A. Mohamed
(74) *Attorney, Agent, or Firm*—Oblon, Spivak, McClelland, Maier & Neustadt, P.C.

(57) ABSTRACT

The present invention provides an artificial chaperon useful for refolding the proteins having low voluntary folding ability and being difficult or unable to be a native form without a second (or assistant) of a molecular chaperon in a short time, and folding said proteins as an active form. The present invention relates to an artificial chaperon kit characterized in that the kit comprises cyclic saccharide cycloamylose and polyoxyethylenic detergent or cyclic saccharide cycloamylose and ionic detergent. The present invention also relates to a method for diluting the denaturant making the protein a denatured state by adding a specific detergent to a denatured protein, and preventing protein molecules from aggregation, thereafter adding cyclic saccharide cycloamylose, utilizing the inclusion ability thereof to strip detergent, accelerating the proper folding of protein into a correct higher-order structure with activity.

22 Claims, 2 Drawing Sheets

ARTIFICIAL CHAPERON KIT

FIELD OF THE INVENTION

The present invention relates to an artificial chaperon kit and the use thereof, more specifically to an artificial chaperon kit comprising of a cycloamylose which is one of cyclic saccharides (hereinafter referred as cyclic saccharide cycloamylose) and a specific detergent and the use thereof. In more detail, the present invention relates to an artificial chaperon kit comprising a cyclic saccharide cycloamylose and a polyoxyethylenic detergent or an artificial chaperon kit comprising a cyclic saccharide cycloamylose and an ionic detergent, as well as a method for refolding denatured protein into native state having an activity by using the artificial chaperon kit.

BACKGROUND OF THE INVENTION

Protein is of a stereoscopic conformation called as higher-order structure, and it is essential for function of a protein to be of a correct higher-order structure. Of these higher-order structures, α-helical structure, β-sheet structure etc. are known as secondary structures, and the protein of thus mentioned secondary structure is further folded to form a tertiary and quaternary structure. As factors for stabilizing the tertiary structure, hydrophobic bond, hydrogen bond, S—S bond between cysteine residues etc. are included.

This higher-order structure is destroyed by physical causes such as heating, freezing, ultraviolet radiation and irradiation of X-ray, as well as by chemical causes such as extreme acid and base, organic solvent, denaturant such as urea and guanidine hydrochloride, and detergent, and converts from orderly folded compact structure to a random coil which is unfold state.

Folding in which the protein of above-mentioned denatured state is refolded to the condition having a correct higher-order structure has two stepwise problems which must be solved. That is, the first step problem is to prevent aggregation between proteins, and the second step problem is how to fold correctly from unfolded state.

In an organism, a class of second (or assistant) proteins a named as molecular chaperon participates in these two steps. Molecular chaperon is a protein having functions of binding to a protein just synthesized to stop misfolding to keep the protein in the state that it is easily carried, and helping the protein which can not be folded well to be folded.

Recently, a trial is reported aiming at constructing an artificial chaperon which mimics a molecular chaperon to solve above two problems.

Daugherty et al. (J. Biol. Chem., vol. 273, No. 51, p.33961–33971 (1998)) has reported a method for refolding a denatured protein into a native structure by using Triton X-100 or polyoxyethylenic detergent having a short chain length of alkyl group detergent, as an artificial chaperon. These two nonionic detergents play a role to prevent proteins from aggregation, and thereafter are removed from the protein-detergent complex in second step.

In this method, β-cyclodextrin (hereinafter, sometimes abbreviated as β-CD), a cyclic saccharide which can accommodate various guest molecules into the hydrophobic cavity, is used as a second (or assistant) agent to strip detergent from protein-detergent complex.

Further, Sivakama Sundari et al. (FEBS Letters, 443, p.215–219 (1999)) shows a method for correctly folding the denatured protein by diluting denatured carbonic anhydrase B (hereinafter, sometimes abbreviated as CAB) and lysozyme with cetyltrimethylammonium bromide (hereinafter, sometimes abbreviated as CTAB) which is a cationic detergent, thereafter acting straight chain dextrin-10 or cyclic β-CD.

However, in any method mentioned above, the ratio in which denatured inactive protein is refolded into the native form is only about 60 to 70%, and β-CD has a problem concerning stability that, such as, low solubility in water and unstableness of solution because of aging, and is not satisfactory for using as a perfect artificial chaperon.

Also, there has been a trial for refolding a denatured protein by dilution dialysis method wherein a denaturant is slowly removed from the protein in denatured state, but applicable proteins are limited: to those having a voluntary folding ability such that the protein spontaneously refolds to the native form even without any special treatment.

Thus, it is an actuality that all of the above-mentioned trials have a problem in that the ratio that the protein is folded as the native form is low, and that the trials can not be applied to the proteins which have a low voluntary folding ability and can not be of a native form without a second (or assistant) of a molecular chaperon.

SUMMARY OF THE INVENTION

It is an object of the invention to solve the above-mentioned problems, and to construct an artificial chaperon useful for refolding the proteins having low voluntary folding ability and being difficult or unable to be a native form without a second (or assistant) of a molecular chaperon, and folding the proteins as an active form.

Therefore, the present inventors paid attention to the fact that there is a large difference of the ability to keep the protein in a dispersed state among a variety of nonionic detergents because of the difference of the structure of sugar of a hydrophilic part or polyoxyethylene, or the length of alkyl group, and examined as to a detergent useful for an artificial chaperon functioning to the first step of folding (prevent protein from aggregation).

Moreover, the present inventors paid attention to the fact that a cyclic saccharide uptakes a variety of guest molecules into the hydrophobic cavity thereof to form an inclusion compound, and examined whether the inclusion ability thereof can be used for the artificial chaperon. However, though β-CD has an excellent inclusion ability, β-CD has a problem in that the aqueous solution thereof is unstable because of low solubility and aging.

Accordingly, we paid attention to the fact that cycloamylose, a larger cyclic saccharide having an inclusion ability similarly to β-CD, has properties of high solubility in water and not aging, H and examined as to the condition for functioning as an artificial chaperon acting to the second step of folding (refolding to the native form).

Consequently, as mentioned above, we found that the combination of cyclic saccharide cycloamylose and polyoxyethylenic detergent, or the combination of cyclic saccharide cycloamylose and ionic detergent, is useful as an artificial chaperon, and reached the present invention.

According to the first aspect of the present invention, there is provided an artificial chaperon kit characterized in that the kit comprises cyclic saccharide cycloamylose and polyoxyethylenic detergent.

According to the second aspect of the present invention, there is provided an artificial chaperon kit characterized in that the kit comprises cyclic saccharide cycloamylose and ionic detergent.

According to the third aspect of the present invention, there is provided a method for diluting the denaturant making the protein a denatured state by adding an excess amount of polyoxyethylenic detergent to a denatured protein consisting of α-helical structure in native state, and preventing protein molecules from aggregation, thereafter adding cyclic saccharide cycloamylose, utilizing the inclusion ability thereof to strip the detergent from protein-detergent complex, assisting proper protein refolding into a native state with activity.

According to the fourth aspect of the present invention, there is provided a method for diluting the denaturant making the protein a denatured state by adding an excess amount of ionic detergent to a denatured protein consisting of β-sheet structure and/or a denatured and reduced protein having an intramolecular S—S bond in native state, and preventing protein from aggregation, thereafter adding cyclic saccharide cycloamylose, utilizing the inclusion ability thereof to remove the detergent from protein-detergent complex, assisting proper protein folding into a native state with activity.

According to the fifth aspect of the present invention, there is provided the artificial chaperon kit as described in the first aspect of the invention, wherein the polyoxyethylenic detergent is polyoxyethylenesorbitan ester, polyoxyethylenedodecyl ether, polyoxyethyleneheptamethylhexyl ether, polyoxyethyleneisooctylphenyl ether, polyoxyethylenenonylphenyl ether, polyoxyethylene fatty acid ester or sucrose fatty acid ester.

According to the sixth aspect of the present invention, there is provided the artificial chaperon kit as described in the second aspect of the invention, wherein the ionic detergent is cetyltrimethylammonium bromide, sodium dodecyl sulfate, sodium deoxycholate, 3-[(3-colamidopropyl)dimethylammonio]-1-propanesulfonic acid, hexadecyltrimethylammonium bromide or myristylsulfobetaine.

According to the seventh aspect of the present invention, there is provided the artificial chaperon kit as described in the first aspect of the invention, wherein the cyclic saccharide cycloamylose is the cyclic saccharide cycloamylose having a polymerization degree of from 25 to 50 or from 40 to 150.

According to the eighth aspect of the present invention, there is provided the artificial chaperon kit as described in the second aspect of the invention, wherein the cyclic saccharide cycloamylose is the cyclic saccharide cycloamylose having a polymerization degree of from 40 to 150.

Figure 1:
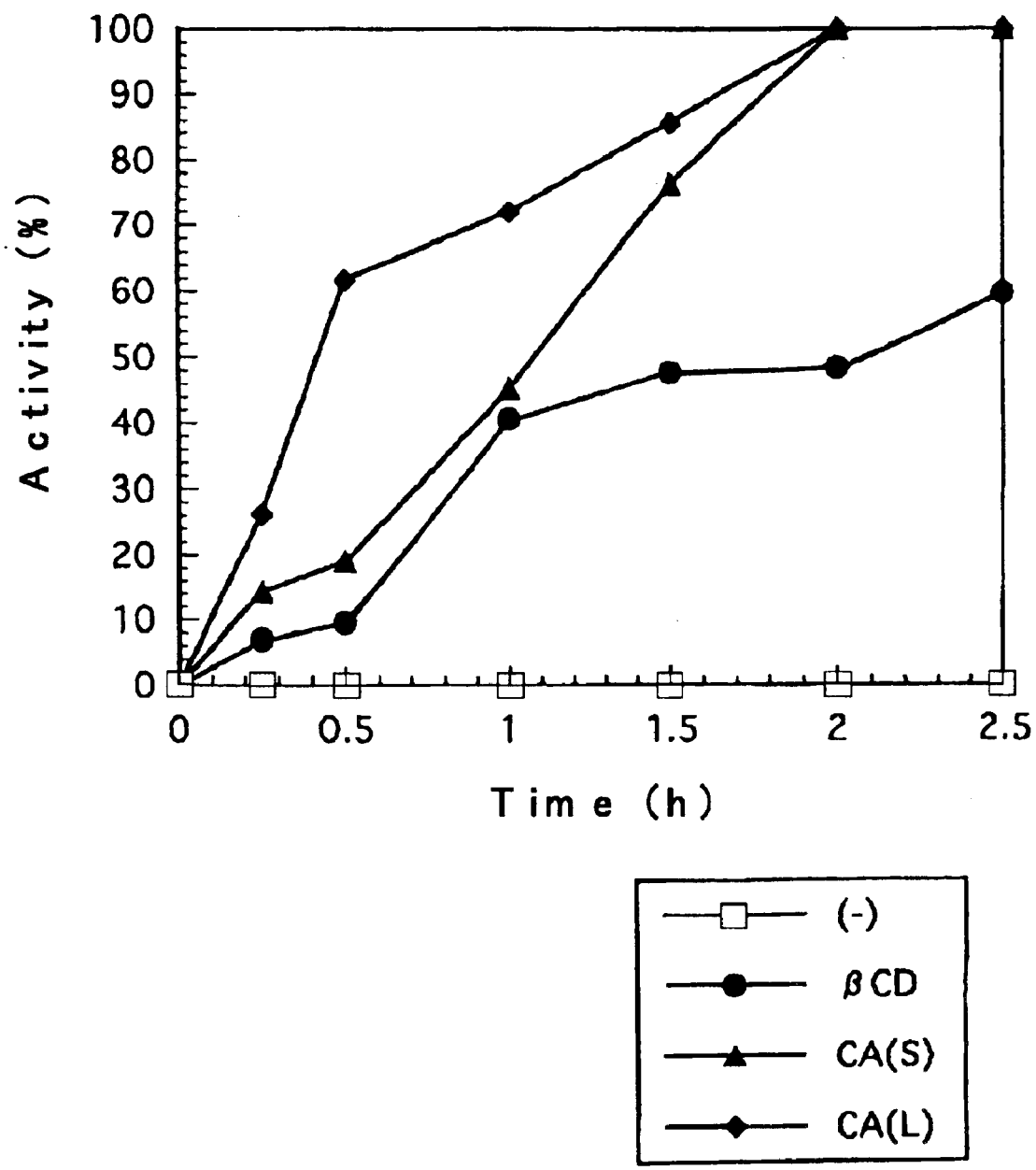
FIG. 1 shows the time course of recovered enzymatic activity by the cyclic saccharide where Tween 40 (having an alkyl group length of 16) is used as the detergent.

In the figures, □ represents a control without addition of detergent and cyclic saccharide, ● represents β-CD, ▲ represents a cyclic saccharide cycloamylose having a polymerization degree of 25 (CA(S)), and ♦ represents a cyclic saccharide cycloamylose having a polymerization degree over 40 (CA(L)).

DETAILED DESCRIPTION OF THE INVENTION

The present inventors selected three kinds of proteins, citrate synthase wherein most of the secondary structure is consisting of α-helical structure in native state (hereinafter, sometimes abbreviated as CS), carbonic anhydrase B wherein nearly 80% of the secondary structure is O-sheet structure in native state (hereinafter, sometimes abbreviated as CAB), and lysozyme containing both α-helical structure and β-sheet structure in native state, and having intramolecular S—S bond, as model proteins in order to construct an artificial chaperon of the object.

These have α-helical structure, β-sheet structure and intramolecular S—S bond which are typical higher-order structures of proteins, and further, have a low voluntary folding ability, and it is difficult to refold without a second (or assistant) of molecular chaperon etc. Therefore, we considered that an artificial chaperon which can refold these three model proteins from the denatured state so that they are of a correct higher-order structure, and can refold into native state having an activity, is applicable to many proteins, and is suitable for constructing an artificial chaperon which is excellently general-purpose.

Therefore, we examined as to the condition for perfectly denaturing these three model proteins by guanidine hydrochloride which is a strong denaturant, and making them refolding and recovering their activity by a combination of a variety of detergents and cyclic saccharides.

As a result of it, we found that the combination of a cyclic saccharide cycloamylose having a polymerization degree of from 25 to 50 (CA(S)) or a polymerization degree of from 40 to 150 (CA(L)) and polyoxyethylenic detergent or the combination of a cyclic saccharide cycloamylose having a polymerization degree of from 40 to 150 (CA(L)) and ionic detergent, acts excellently as an artificial chaperon, refolds the denatured CS to a native structure in a short time, and recovers the activity perfectly.

From the above, it has become clear that a kit comprising a specific cyclic saccharide cycloamylose and a detergent is suitable for an artificial chaperon.

In the present invention, polyoxyethylenic or ionic detergent is used for an artificial chaperon in order to prevent protein from aggregation in the first step of refolding, and a cyclic saccharide cycloamylose is used as an artificial chaperon to remove the detergent from the protein-detergent complex by the inclusion ability and assist the proper protein folding into a native state in the second step.

Then, we examined more concretely as to an artificial chaperon, which can be used for model protein such as CS.

First, in order to make the model protein CS denatured state, CS is denatured by guanidine hydrochloride. That is, guanidine hydrochloride solution prepared so that the final concentration is 6M is added to CS, allow to stand for 1 hour or more at room temperature, thereby make it a denatured protein in the state wherein the higher-order structure is released to be unfolded. This denatured model protein retains no enzymatic activity.

The model protein in the denatured state is considered to be a nascent protein which is not of the stereoscopic structure right after the translation in the organism. The nascent protein is bound a group of molecular chaperon acting in the upstream of the folding process named as DnaJ etc. in order to prevent aggregation and abnormal structure right after the termination of the translation.

In the present invention, a detergent is used as an artificial chaperon playing this role. 70 volumes of detergent solution is added to 1 volume of model protein solution in denatured state, and allow to stand for 1 hour at room temperature. In the technique called as dilution dialysis method, the protein in denatured state is refolded to native structure by gradually removing the denaturant (guanidine hydrochloride, urea, etc.) from the protein in denatured state, but, in this case, the problem arise that the protein aggregates as the denaturant is removed, etc.

Therefore, by functioning the detergent as an artificial chaperon acting in the upstream in the process of folding, the problem can be solved that the protein aggregates when the denaturant is diluted by a large excess amount of the solution.

A function as an artificial chaperon is discussed as to a number of nonionic detergents. As a result of it, for a denatured protein having α-helical structure, of nonionic detergents, the polyoxyethylenic detergent represented by the general formula $C_nH_{2n+1}(OCH_2CH_2)_xOH$ and usually abbreviated as $C_nE_x$, preferably, polyoxyethylenesorbitan ester, polyoxyethylenedodecyl ether, polyoxyethyleneheptamethylhexyl ether, polyoxyethyleneisooctylphenyl ether, polyoxyethylenenonylphenyl ether, polyoxyethylene fatty acid ester, or sucrose fatty acid ester, is used. Further, nonionic detergent, such as octylglucoside, heptylthioglucoside, decanoyl-N-methylglucamide can be used. Moreover, the detergent is dissolved in an appropriate buffer, and used as a solution.

Of the above polyoxyethylenic detergents, polyoxyethylenesorbitan ester is abbreviated as $C_n$ sorbitan $E_x$, and those having a polyoxyethylene chain length of 20 are suitably used. Specifically, Tween 20, 40, 60, 80 (purchased from Atlas Powder or Sigma) etc. correspond to this. Especially, Tween 40 and Tween 60 having an alkyl group length of 16 and 18, respectively, are a preferable.

If the polyoxyethylene chain length of the detergent of interest is outside of the above-mentioned range, the ability of keeping the protein in soluble state is reduced, and the effect of preventing the target protein from aggregating can not be obtained enough, so that this is not preferable.

On the other hand, for the modified protein having β-sheet structure or intramolecular S—S bond, an ionic detergent is used as an artificial chaperon functioning in the first step. The ionic detergent is not specifically limited, and includes, for example, cetyltrimethylammonium bromide, sodium dodecyl sulfate, sodium deoxycholate, 3-[(3-colamidopropyl)dimethylammonio]-1-propanesulfonic aid, hexadecyltrimethylammonium bromide (hereinafter, sometimes abbreviated as CTAB), and myristylsulfobetaine (hereinafter, sometimes abbreviated as SB3-14), and especially cationic detergent such as CTABSB3-14 is preferable.

Next, as an artificial chaperon playing a role of stripping the above-mentioned detergent by the function of inclusion action, allowing proper folding of protein, regardless of the pattern of the higher-order structure of the denatured protein, that is, in any case of the model protein, a cyclic saccharide cycloamylose is used. Cycloamylose (CA) has an excellent property that it has a high solubility in water, and is not aged while being a cyclic CD saccharide having an inclusion ability. Moreover, for a denatured protein having α-helical structure, the equivalent effect can be obtained even when β-CD is used instead of CA.

While cyclic saccharide cycloamylose having a variety of polymerization degree is known, in the present invention, that having a polymerization degree of from 25 to 50, that is, CA(S) or that having a polymerization degree of from 40 to 150, that is, CA(L) is used. When nonionic detergent such as polyoxyethylenic detergent is used as the above-mentioned detergent, both CA(S) and CA(L) can be used. When ionic detergent is used as the detergent, CA(L) is used.

The above-mentioned nascent protein begins to fold into proper structure possessing an acitivity by the function of the molecular chaperon acting in the downstream named as GroE as the process of the folding further progresses, and in this process, the molecular chaperon which has acted as a second (or assistant) goes away.

It is a cyclic saccharide cycloamylose that functions similarly to this molecular chaperon. This has an inclusion ability, and uptakes the above-mentioned detergent making the protein-detergent complex and preventing the protein from being in an abnormal structure, such as aggregation, into the hydrophobic cavity of itself to form an inclusion compound.

Consequently, the detergent is gradually removed from the protein-detergent complex, and the protein is refolded to the native state slowly, and recovered the activity. In either case where CA(S) or CA(L) is used, the protein perfectly recovers its activity within 2 hours after the addition of CA(S) or CA(L).

The yield of refolding of the protein by the artificial chaperon can be evaluated by assaying the activity of the protein. Here, the method for assaying the activity of the protein includes calorimetric quantitation method (acetylcoenzyme method, ρNPA esterase method), bacteriolytic activity method etc. Moreover, the aggregation state of the protein can be confirmed by light scattering, and whether the stereoscopic structure is formed or not can be confirmed by circular dichroism.

As in the present invention, an artificial chaperon of the combination of a cyclic saccharide cycloamylose and a specific detergent can function effectively to a variety of model proteins having different higher-order structure, and is general-purpose. Therefore, this artificial chaperon is expected to be used for refolding system of a number of beneficial protein having a problem in the expression system such as inclusion body is formed.

The artificial chaperon kit of the present invention has an excellent property that it can refold the protein which has a low voluntary folding ability and which can not be of the correct higher-order structure without a second (or assistant) of a molecular chaperon in a short time so that the protein can be of the correct higher-order structure, and the ratio that the kit folds the protein into the active form is high.

EXAMPLES

Hereinafter, the present invention is explained in detail by examples etc., but the present invention is not limited thereto.

Example 1

Determination of the Refolding Yield of a Model Protein Containing Mainly α-Helical Structure in Native State, CS In the present example, the combination of detergent and cyclic saccharide effectively functioning as the artificial chaperon was examined as to refolding of CS, which is a model protein composed of α-helical structure.

(1) Preparation of Denatured CS

Denaturation of citrate synthase (CS) is conducted according to the following procedure by the conventional method using guanidine hydrochloride.

First, native CS (purchased from Beringer Mannheim) was dissolved in guanidine hydrochloride solution, and reacted for 1 hour at 25° C., thereby the higher-order structure of CS was destroyed, and the denatured protein solution wherein the enzymatic activity was perfectly lost was prepared. Moreover, the CS concentration of the denatured solution was 2.4 mg/mL, and the concentration of guanidine hydrochloride was 6 M, and the concentration of dithiothreitol was 40 mM.

(2) Method for Refolding

The detergent buffer was prepared so as to be 0.1% detergent, 0.71 mM EDTA, 145 mM Tris-HCl buffer (pH 7.6) when used. This freshly prepared detergent buffer was added in the ratio of 70 volumes to 1 volume of the denatured CS solution of above (1), and allowed to stand for 1 hour at room temperature.

20 volumes of cyclic saccharide cycloamylose solution (16 mM) was added to 80 volumes of detergent-CS complex solution thus formed, and incubated overnight at 25° C.

After overnight reaction, the resulting aggregate was removed by passing through cellulose acetate filter having a pore size of 0.2 μm as the pretreatment, thereafter the enzymatic activity was assayed.

Moreover, in the present example, in order to examine refolded yield of the denatured protein with the passage of time, small amounts of the reaction solution were taken at different time intervals, and these were pretreated the same as the above, thereafter the enzymatic activity was assayed.

(3) Assay of Enzymatic Activity

Figure 2:
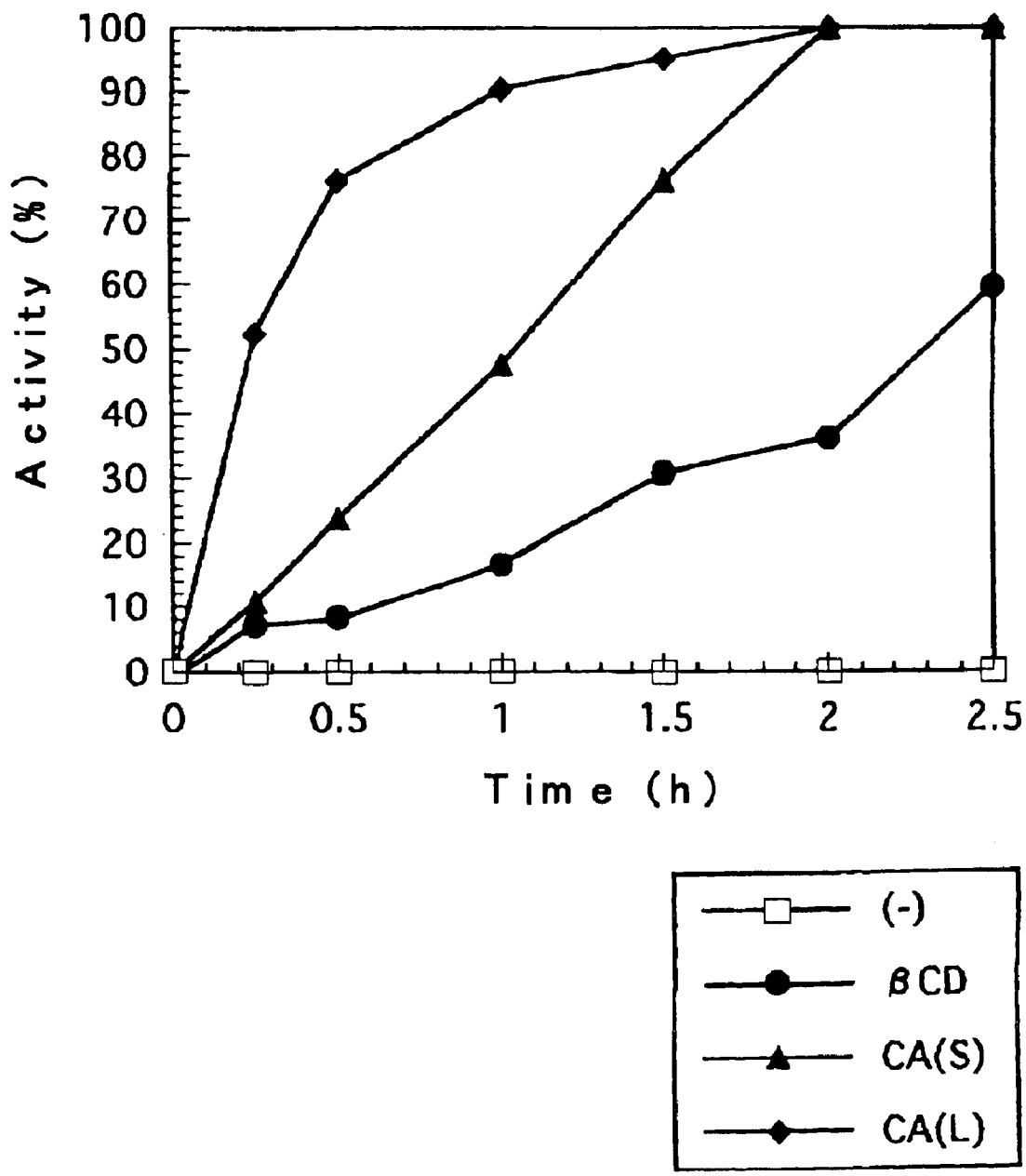
FIG. 2 shows the time course of recovered enzymatic activity by the cyclic saccharide where Tween 60 (having an alkyl group length of 18) is used as the detergent.

20 μL of the refolded CS solution obtained in the above (2) or native CS was added to 380 μL of the reaction solution wherein acetyl CoA and oxaloacetic acid was dissolved as substrates, and the increase in absorbance at 412 nm at 25° C. was measured every 0.5 second for 60 seconds using a spectrophotometer. From this, the initial rate of the reaction was calculated. The yield of refolded CS was determined by comparing the resulting initial rate with that in of native enzyme. Moreover, the composition of the substrate solution was 150 mM Tris-HCl buffer (pH 7.6), 0.022 μM acetyl CoA, 0.48 mM oxaloacetic acid, 0.11 mM dithiobis as the final concentration at the time of reaction. The recovery of the enzymatic activity of CS is shown in Table 1. The enzymatic activity was expressed as 100% when native CS was diluted by the above-mentioned buffer so that the concentration thereof becomes the same. Moreover, FIG. 1 shows the time course of recovery of an enzymatic activity by the cyclic saccharide where Tween 40 (having an alkyl group length of 16) is used as the detergent, and FIG. 2 shows the time course of recovery of an enzymatic activity by the cyclic saccharide where Tween 60 (having an alkyl group length of 18) is used as the detergent.

TABLE 1

|  |  | ⊕CD | β - CD | γ CD | CA (S) | CA (L) |
|---|---|---|---|---|---|---|
| Ionic | CTAB | 40 | 20 | 5 | 10 | 5 |
|  | SB3-14 | 20 | 40 | (-) | (-) | 10 |
| Nonionic |  |  |  |  |  |  |
| CnEx | C12E6 | 12 | 20 | (-) | (-) | 25 |
|  | C12E8 | 10 | 10 | (-) | (-) | 20 |
|  | C12E10 | 30 | 50 | (-) | (-) | 30 |
|  | Brij 30 | 8 | 8 | (-) | 8 | 2 |
|  | Brij 35 | (-) | 50 | 30 | (-) | 40 |
|  | Brij 56 | (-) | (-) | (-) | (-) | (-) |
|  | Brij 58 | 8 | 6 | (-) | 4 | 2 |
|  | Brij 78 | 8 | 1 | (-) | (-) | (-) |
|  | Brij 96 | (-) | (-) | (-) | (-) | (-) |
|  | Lubrol PX | 40 | 60 | (-) | 15 | (-) |
| Cn φ Ex | TritonX-100 | (-) | 60 | 40 | 6 | 3 |
|  | NP 40 | (-) | 50 | 40 | (-) | (-) |
| Cn sorbitan Ex | Tween 20 | 30 | 60 | 30 | 80 | 60 |
|  | Tween 21 | (-) | (-) | (-) | (-) | (-) |
|  | Tween 40 | 50 | 120 | 8 | 140 | 120 |
|  | Tween 60 | 70 | 130 | 8 | 140 | 120 |
|  | Tween 80 | 60 | 90 | (-) | 100 | 100 |
|  | Tween 81 | 15 | 20 | 15 | 20 | 15 |
|  | Emalgen 810 | (-) | (-) | (-) | (-) | (-) |
|  | Emalgen 911 | (-) | 40 | 30 | (-) | (-) |

*(-) Almost no activity

As shown in Table 1, among a variety of ionic and nonionic detergents, the combination of alkylpolyoxyethylene ether which is a nonionic detergent and β-CD, CA(S) or CA(L) was effective as an artificial chaperon. Among others, of acyl polyoxyethylenesorbitan ester ($C_n$ sorbitan $E_x$), that having a polyoxyethylene chain length of 20 is effective, concretely, Tween 20, 40, 60, 80 (manufactured by Atlas Powder or Sigma) correspond to this, and the best chaperon is the combination of Tween 40 and Tween 60 having an alkyl group length of 16 and 18 respectively and CA(S) or CA(L), and it became clear that the combination recovered 100% of activity.

Moreover, as to the change with the passage of time of the enzymatic activity, as apparent from FIGS. 1 and 2, it has become clear that, in case of the artificial chaperon using CA(S) and CA(L) as the cyclic saccharide, the enzyme was refolded into the active form within as short as 2 hours after the addition of cycloamylose. That is, this shows that the artificial chaperon of the present invention has the ability of refolding the denatured protein in unfolded state correctly within a short time.

On the other hand, in case of β-CD, only from about 30 to 40% of the enzymatic activity was recovered 2 hours after the addition of the β-CD, and it took more than overnight to recover 100% of the enzymatic activity.

Therefore, it has become clear that cycloamylose is more preferable agent used as the artificial chaperon of the present invention.

Moreover, when native CS was allowed to stand for several days, the enzymatic activity was decreased, whereas the CS refolded by the artificial chaperon of the present invention did not show the decrease of the activity even after it was allowed to stand for 6 days at room temperature.

Example 2

Determination of the Refolding Yield of CAB which is the Model Protein Constructing Nearly 80% of β-Sheet Structure in Native State (1) Preparation of Denatured CAB CAB (purchased from Sigma) was denatured by the following procedure using guanidine hydrochloride according to the conventional method.

First, the higher-order structure of CAB was destroyed by adding solution of CAB (30 mg/mL) to 6M of guanidine hydrochloride and reacted at 25° C. for 16 hours, and guanidine hydrochloride denatured CAB was completely lost its activity.

(2) Method for Refolding

The detergent buffer was prepared so as to be 0.1% detergent, 23 mM Tris-sulfuric acid buffer (pH 7.8) when used. As the detergent, CTAB, SB3-14, Tween 40, 60 (purchased from Atlas Powder or Sigma) were used.

The freshly prepared detergent buffer was added to denatured CAB solution of above (1) in the ratio of 700 volumes to 1 volume of CAB solution, and allow to stand for 10 minutes at room temperature to form detergent-CAB complex.

Next, 16 mM of cyclic saccharide solution which was separately prepared was added in the ratio of 15 volumes to 35 volumes of the detergent-CAB complex solution, and incubated overnight at 25° C.

After overnight reaction, the aggregate in the reaction solution was removed by passing through cellulose acetate filter having a pore size of 0.2 μm as the pretreatment. Thereafter, the enzymatic activity was determined in the same manner as Example 1.

(3) Assay of CAB Activity

450 μL of refolded CAB solution obtained in the above (2) or native CAB was added to 50 μL of the reaction solution wherein paranitrophenylacetate (pNPAC) was dissolved as the substrate, and the increase in absorbance at 400 nm at 25° C. was measured every 0.5 second for 60 seconds using a spectrophotometer. From this, the initial rate of the reaction was calculated, and the refolding yield was determined the same as on Example 1. The composition of the substrate solution was 52 mM pNPAC, 23 mM Tris-sulfuric acid buffer (pH 7.8) as the final concentration at the time of reaction. The recovery of CAB activity after overnight reaction with the cyclic saccharide is shown in Table 2. Moreover, the enzymatic activity was expressed as 100% when native CAB was diluted by the above-mentioned buffer so that the concentration thereof becomes the same.

TABLE 2

|  |  | αCD | β - CD | γ CD | CA (S) | CA (L) |
| --- | --- | --- | --- | --- | --- | --- |
| Ionic | CTAB | 10 | 56 | 63 | 53 | 100 |
|  | SB3-14 | 25 | 60 | 44 | 47 | 88 |
| Nonionic | Tween 40 | — | 53 | — | 47 | 40 |
|  | Tween 60 | 0 | 6.2 | 8.7 | 2 | 10 |

Consequently, it has become clear that the activity of CAB was recovered 100% by the combination of CTAB which is an ionic detergent and CA(L). On the other hand, preferable effect was not obtained by using SB3-14 which is an ionic detergent and Tween 40 and Tween 60 which are nonionic detergents.

From the fact that the result in the present Example is completely different from the result in Example 1 in which CS was used as the model protein, it has been shown that it is necessary to establish the artificial chaperon corresponding to the higher-order structure of the protein which is the object of refolding.

Example 3

Determination of the Refolding Yield of Lysozyme which is the Model Protein Constructing Both α-Helical Structure and β-Sheet Structure and Having Intramolecular S—S Bond in Native State 1) Preparation of Denatured and Reduced Lysozyme Denaturation and reduction of lysozyme was carried out according to the following procedure by the conventional method using guanidine hydrochloride and dithiothreitol.

Lysozyme solution was added to guanidine hydrochloride solution containing dithiothreitol and incubated for 16 hours at 25° C., and the higher-order structure of lysozyme was destroyed, so that the enzymatic activity was completely lost. Moreover, the concentrations of the each component in the denatured solution were 15 mg/mL lysozyme, 5 M guanidine hydrochloride, and 50 mM dithiothreitol.

(2) Method for Refolding

CTAB was used as the detergent, and the detergent buffer was prepared so as to be 0.1% CTAB, 2 mM DL-cystine, 23 mM Tris-acetic acid buffer (pH 8.1) when used.

The freshly prepared detergent buffer was added in the ratio of 100 volumes to 1 volume of denatured/reduced lysozyme solution obtained in the above (1) and allowed to stand 1 hour at room temperature, thereby detergent-lysozyme complex was formed.

Then, 16 mM of cyclic saccharide solution which was separately prepared was added in the ratio of 60 volumes to 140 volumes of the detergent-lysozyme complex, and incubated overnight at 25° C.

After overnight incubation, the aggregate in the reaction solution was removed by passing through cellulose acetate filter having a pore size of 0.2 μm as the pretreatment. Thereafter, the enzymatic activity was determined in the same manner as Example 1.

(3) Assay of Lysozyme Activity

20 μL of the reaction solution containing refolded lysozyme solution obtained in the above (2) was added to 500 μL of the reaction solution in which *Micrococcus lysodeikticus* was suspended as the substrate, and the decrease in absorbance at 450 nm at 25° C. was measured every 0.5 second for 60 seconds using a spectrophotometer. From this, the initial rate of the reaction was calculated and the refolding yield was determined the same as on Example 1. The composition of the substrate solution was 0.16 mg/mL *Micrococcus lysodeikticus,* 50 mM phosphate buffer (pH 6.2) as the final concentration at the time of reaction. The refolding yield of lysozyme after reacted with cyclic saccharide overnight is shown in Table 3. The enzymatic activity was expressed as 100% when native lysozyme was diluted by the above-mentioned buffer so that the concentration thereof becomes the same.

TABLE 3

|  | β - CD | CA (S) | CA (L) |
| --- | --- | --- | --- |
| CTAB | 80 | 80 | 95 |

As shown in Table 3, it has become clear that the combination of CTAB which is an ionic detergent and CA(L) functions effectively as the artificial chaperon. Lysozyme modified in the present Example has intramolecular S—S bond between cysteine residue as a higher-order structure, and it has become clear that, though the bond was broken by dithiothreitol which is a reducing agent, the enzymatic activity is recovered 80% by acting the artificial chaperon of the present invention in the presence of DL-cystine.

This shows that even the protein having intramolecular S—S bond has the higher-order structure can be refolded from inactive denatured/reduced state to active state by designing an appropriate artificial chaperon.

What is claimed is:

1. A kit for refolding denatured protein, comprising (a) a cyclic saccharide cycloamylose having a degree of polymerization of 25 to 150 and (b) a polyoxyethylenic detergent or a sucrose fatty acid ester detergent.

2. The kit of claim 1, wherein the polyoxyethylenic detergent is selected from the group consisting of polyoxyethylenesorbitan ester, polyoxyethylenedodecyl ether, polyoxyethyleneheptamethylhexyl ether, polyoxyethyleneisooctylphenyl ether, polyoxyethylenenonylphenyl ether, polyoxyethylene and fatty acid ester.

3. The kit of claim 1, wherein the cyclic saccharide cycloamylose has a polymerization degree of from 25 to 50.

4. The kit of claim 1, wherein the cyclic saccharide cycloamylose has a polymerization degree of from 40 to 150.

5. A kit for refolding denatured protein, comprising (a) a cyclic saccharide cycloamylose having a polymerization degree of from 25 to 150 and (b) an ionic detergent.

6. The kit of claim 5, wherein the cyclic saccharide cycloamylose has a polymerization degree of from 25 to 50.

7. The kit of claim 5, wherein the cyclic saccharide cycloamylose has a polymerization degree of from 40 to 150.

8. The kit of claim 5, wherein the ionic detergent is selected from the group consisting of cetyltrimethylammonium bromide, sodium dodecyl sulfate, sodium deoxycholate, 3-[(3-colamidopropyl)dimethylamino]-1-propane sulfonic acid, hexadecyltrimethylammonium bromide and myristylsulfobetaine.

9. A method of refolding a denatured protein, comprising:
    contacting a polyoxyethylenic detergent or a sucrose fatty acid ester detergent with a denatured protein to from a protein/detergent complex, followed by contacting the protein/detergent complex with a cyclic saccharide cycloamylose hag a degree of polymerization of 25 to 150, to produce a folded protein.

10. The method of claim 9, wherein the polyoxyethylenic detergent is selected from the group consisting of polyoxyethylenesorbitan ester, polyoxyethylenedodecyl ether, polyoxyethyleneheptamethylhexyl ether, polyoxyethyleneisooctylphenyl ether, polyoxyethylenenonylphenyl ether, polyoxyethylene and fatty acid ester.

11. The method of claim 9, wherein the cyclic saccharide cycloamylose has a polymerization degree of from 25 to 50.

12. The method of claim 9, wherein the cyclic saccharide cycloamylose has a polymerization degree of from 40 to 150.

13. The method of claim 9, wherein the folded protein comprises an α-helical structure.

14. The method of claim 9, wherein the folded protein comprises an β-sheet structure.

15. The method of claim 9, wherein the refolded protein comprises an intramolecular S—S bond.

16. A method of refolding a denatured protein, comprising:
    contacting an ionic detergent with a denatured protein to from a protein/detergent complex, followed by
    contacting the protein/detergent complex with a cyclic saccharide cycloamylose having a degree of polymerization of 25 to 150, to produce a folded protein.

17. The method of claim 16, wherein the cyclic saccharide cycloamylose has a polymerization degree of from 25 to 50.

18. The method of claim 16, wherein the cyclic saccharide cycloamylose has a polymerization degree of from 40 to 150.

19. The method of claim 16, wherein the folded protein comprises an α-helical structure.

20. The method of claim 16, wherein the folded protein comprises an β-sheet structure.

21. The method of claim 16, wherein the refolded protein comprises an intramolecular S—S bond.

22. The method of claim 16, wherein the ionic detergent is selected from the group consisting of cetyltrimethylammonium bromide, sodium dodecyl sulfate, sodium deoxycholate, 3-[(3-colamidopropyl)dimethylamino]-1-propane sulfonic acid, hexadecyltrimethylammonium bromide and myristylsulfobetaine.

\* \* \* \* \*